(12) United States Patent
Li et al.

(10) Patent No.: US 6,736,829 B1
(45) Date of Patent: May 18, 2004

(54) TOGGLE ANCHOR AND TOOL FOR INSERTION THEREOF

(75) Inventors: Lehmann K. Li, Milford, CT (US); Ernie Corrao, Bethel, CT (US)

(73) Assignee: Linvatec Corporation, Largo, FL (US)

( * ) Notice: Subject to any disclaimer, the term of this patent is extended or adjusted under 35 U.S.C. 154(b) by 0 days.

(21) Appl. No.: 09/710,215

(22) Filed: Nov. 10, 2000

Related U.S. Application Data

(60) Provisional application No. 60/164,898, filed on Nov. 11, 1999, and provisional application No. 60/188,894, filed on Mar. 14, 2000.

(51) Int. Cl.⁷ .............................................. A61B 17/04
(52) U.S. Cl. ...................................................... 606/232
(58) Field of Search ....................... 606/232, 72, 67, 606/60

(56) References Cited

U.S. PATENT DOCUMENTS

| | | | |
|---|---|---|---|
| 2,213,715 A | | 9/1940 | Monahan |
| 4,741,330 A | | 5/1988 | Hayhurst |
| 4,759,765 A | | 7/1988 | Van Kampen |
| 4,776,330 A | | 10/1988 | Chapman et al. |
| 4,823,794 A | | 4/1989 | Pierce |
| 4,898,156 A | | 2/1990 | Gatturna et al. |
| 5,002,574 A | | 3/1991 | May et al. |
| 5,041,129 A | * | 8/1991 | Hayhurst et al. ............ 606/232 |
| 5,163,946 A | | 11/1992 | Li |
| 5,203,787 A | | 4/1993 | Noblitt et al. |
| 5,217,486 A | | 6/1993 | Rice et al. |
| 5,269,809 A | | 12/1993 | Hayhurst et al. |
| 5,354,298 A | | 10/1994 | Lee et al. |
| 5,372,604 A | | 12/1994 | Trott |
| 5,405,359 A | * | 4/1995 | Pierce ......................... 606/232 |
| 5,443,482 A | | 8/1995 | Stone et al. |
| 5,464,425 A | | 11/1995 | Skiba |
| 5,464,427 A | | 11/1995 | Curtis et al. |
| 5,486,197 A | | 1/1996 | Le et al. |
| 5,522,846 A | | 6/1996 | Bonutti |
| 5,531,792 A | | 7/1996 | Huene |
| 5,540,718 A | | 7/1996 | Bartlett |
| 5,545,180 A | | 8/1996 | Le et al. |
| 5,569,303 A | | 10/1996 | Johnson |
| 5,584,862 A | * | 12/1996 | Bonutti ....................... 606/232 |
| 5,845,645 A | | 12/1998 | Bonutti |
| 5,941,882 A | | 8/1999 | Jammet et al. |
| 6,102,934 A | | 8/2000 | Li |
| 6,117,161 A | | 9/2000 | Li et al. |
| 6,447,516 B1 | * | 9/2002 | Bonutti ........................ 606/72 |

FOREIGN PATENT DOCUMENTS

| | | |
|---|---|---|
| EP | 0270704 | 6/1988 |
| FR | 2622430 | 5/1989 |

* cited by examiner

Primary Examiner—Julian W. Woo
Assistant Examiner—D. Jacob Davis
(74) Attorney, Agent, or Firm—Ostrolenk, Faber, Gerb & Soffen, LLP

(57) ABSTRACT

A method for delivering an anchor member into biological tissue comprising: accessing and preparing an insertion site for the anchor member; holding the anchor member at a distal end of an insertion tool; providing the anchor member to the site with the insertion tool; causing a rotational movement of the anchor member about a first axis perpendicular to a longitudinal axis of the insertion tool whereby the anchor member engages the tissue at the site by moving about the first axis from a first position substantially aligned with the longitudinal axis to a second position at an angle relative to the longitudinal axis; and withdrawing the insertion tool from the site, leaving the anchor member secured at the site.

22 Claims, 6 Drawing Sheets

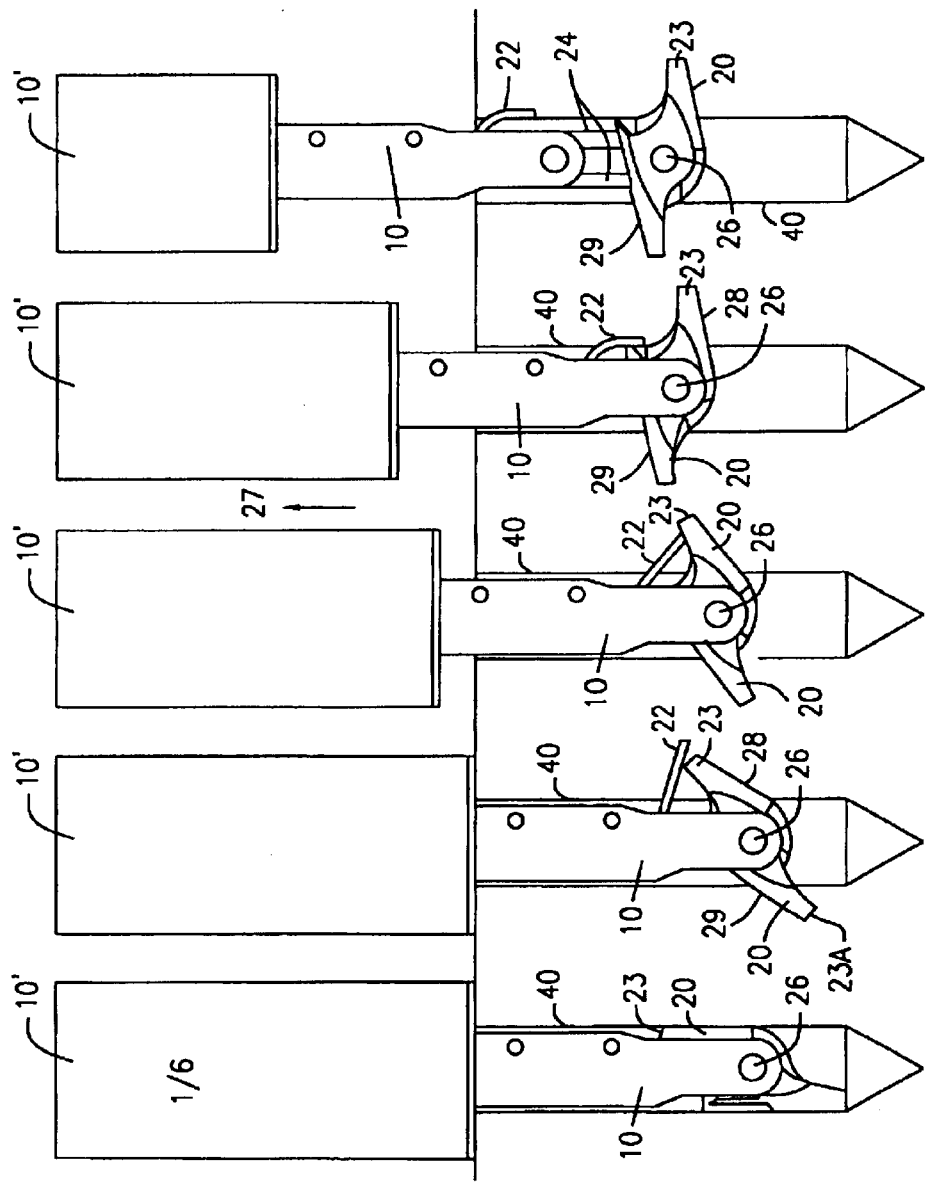

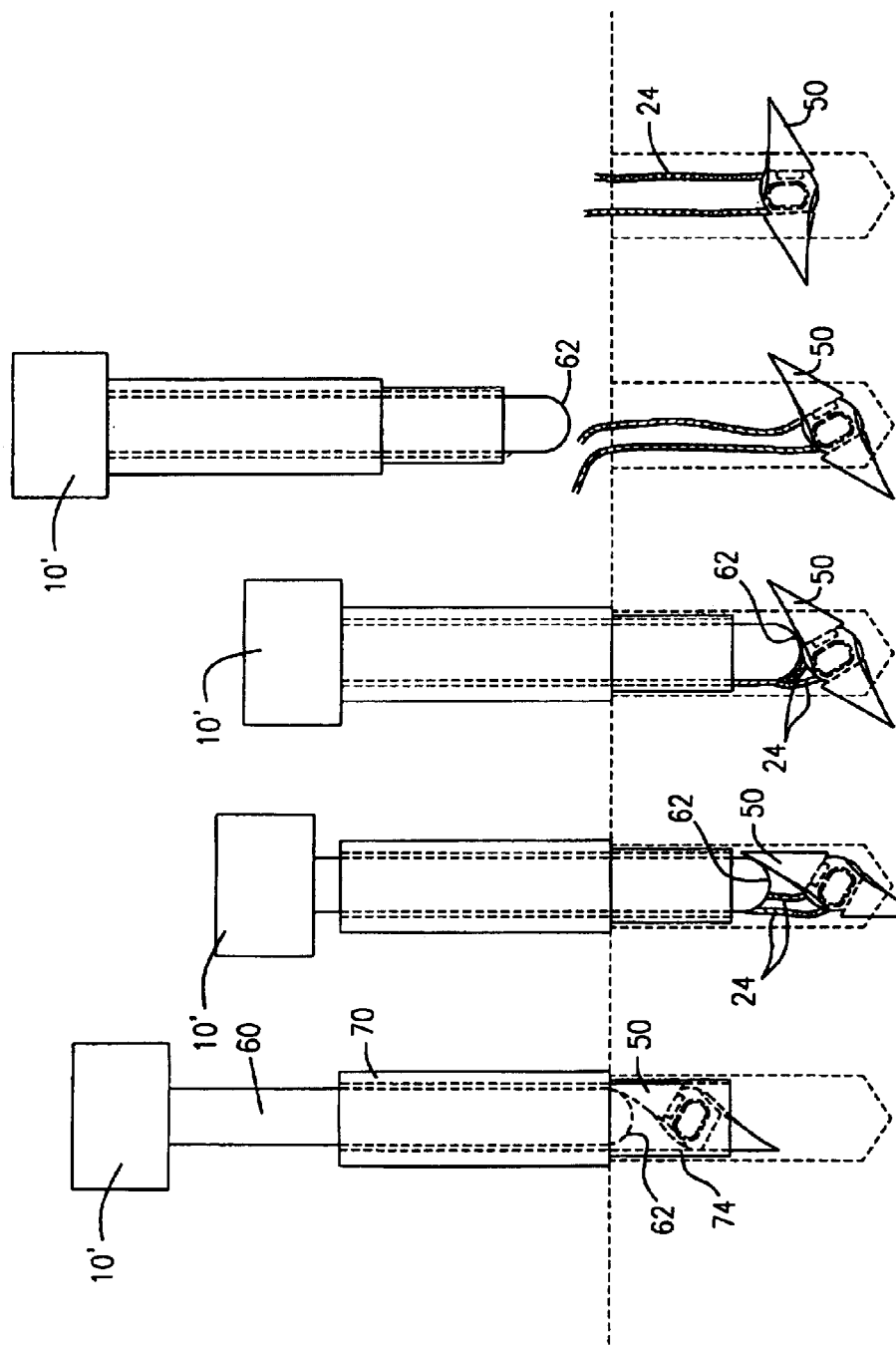

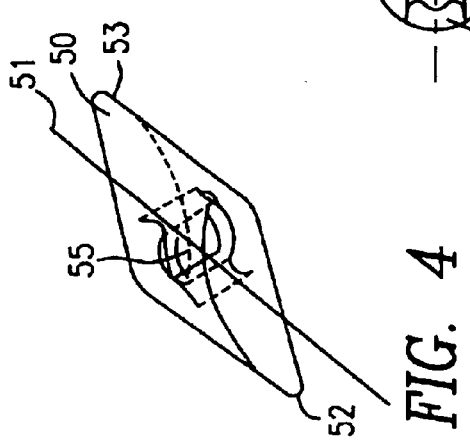
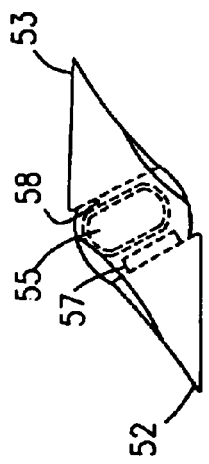
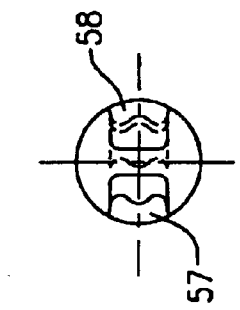
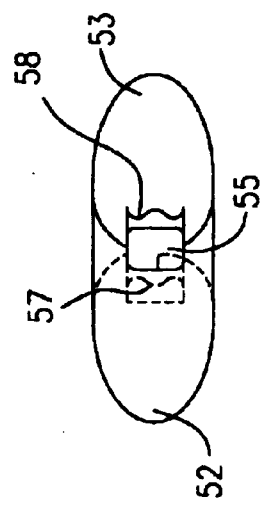
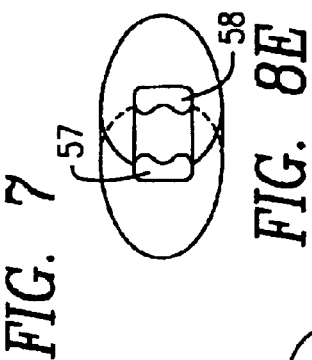
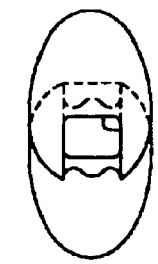
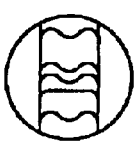
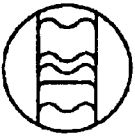

TOGGLE ANCHOR AND TOOL FOR INSERTION THEREOF

REFERENCE TO RELATED APPLICATION

This application claims the benefit and priority of U.S. Provisional application Ser. No. 60/164,898 filed Nov. 11, 1999 and U.S. Provisional application Ser. No. 60/188,894 filed Mar. 14, 2000.

BACKGROUND OF THE INVENTION

The present invention is relates to fixation devices or anchors and tools and methods for emplacing the same. The present invention, in particular, relates to medical anchors, for example, suture anchors or prosthesis anchors. The invention further relates to a method and apparatus for implanting such devices in biological materials, for example bone. Even more particularly, the present invention relates to a medical anchor which can be inserted through a longitudinally or even curved extending bore hole so that the anchor is initially substantially aligned with the bore hole, and then, the emplacement tool manipulated so that the anchor pivots to form an undercut in the bore hole. The present invention is particularly suitable for the emplacement of anchors adapted to repair ligaments, for example rotator cuff ligaments, interior cruciate ligaments (ACL's) and other ligaments. The anchor is also suitable for prosthesis fixation.

In applicant's U.S. Pat. No. 6,117,161, a medical anchor is disclosed which can be emplaced in a groove which extends substantially parallel to the surface of the bone and then rotated along an axis defined by an employment tool and which axis is perpendicular to the extent of the groove to form an undercut in the walls of the groove to secure the anchor.

In applicant's U.S. Pat. No. 6,102,934, a medical anchor is disclosed which can be emplaced in a borehole so that the anchor is initially substantially aligned with the borehole and then, via an emplacement tool, manipulated so the anchor pivots in two axes to form an undercut in the borehole.

In applicant's co-pending U.S. patent application Ser. No. 09/580,777 filed May 26, 2000, a medical anchor is disclosed which can be emplaced in a bore hole so that the anchor is initially substantially aligned with the bore hole and then, using an emplacement tool, rotated about the axis of the tool. A deploy spring causes the anchor to deploy and rotate about an axis perpendicular to the axis of the tool to initially engage the borehole. Further rotation of the tool causes the anchor to cut into the borehole. The rotation by the user and action of the spring causes the anchor to screw into the borehole as it turns on two axes.

Applicant is also aware of U.S. Pat. No. 5,203,787 to Noblitt et al. in which a suture anchor can be emplaced in bone. Applicant is also aware of U.S. Pat. No. 5,569,302 to Johnson for an apparatus and method for attaching an anchor to bone.

The requirement of U.S. Pat. No. 6,117,161 to form a groove into the surface of the bone prior to emplacing the anchor in some instances may be a deficiency. By forming a groove in the bone, the more dense cortical layer of bone is removed, thus compromising the fixation capability of any anchor. Further, the anchor and tool designs of U.S. Pat. No. 6,102,934 and application Ser. No. 09/580,777 filed May 26, 2000 are more complex due to the rotation of the anchor in two axes. Both of these designs typically require a rotational force to be applied to the tool to set the anchor.

Modern trends in surgery include the restoration of bodily function and form, i.e., repair of anatomical structures through the use of minimally invasive surgical techniques. The ability to surgically repair damaged tissues or joints creating as few and as small incisions as possible produces less trauma, less pain and better clinical outcomes in general.

SUMMARY OF THE INVENTION

It is therefore an object of the present invention to provide an apparatus and minimally invasive method for delivering material simply and securely into tissue.

A further object of the invention is provide a method and apparatus for emplacing an anchor into a borehole in substantial alignment with the bore hole and once inserted, activated simply so that it engages with the walls of the borehole by moving to a position substantially at an angle (up to a perpendicular angle) to the borehole.

Such an anchor would be suitable, for example, to repair rotator cuff and other ligament injuries such that the appropriate attachment strength is provided.

It is an object of the invention to provide a method and apparatus to set a surgical anchor with a simple tool motion, preferably without rotation of the emplacement tool.

The present invention comprises an apparatus and method for delivering an anchor member which sets in biological tissue. The apparatus and method for delivering the anchor member into biological tissue comprises the following basic steps:

(a) accessing and preparing the intended insertion sites;

(b) inserting into the site, using an emplacement tool, an anchor member that is set by applying a rotation motion to the anchor member; and (c) after insertion into the site, causing the anchor member to engage the tissue by moving from a substantially in-line position relative to an insertion hole at the site to an angled position with respect to the insertion hole the angled position can be any angle with respect to the insertion hole up to and including an angle that is perpendicular to the insertion hole.

Steps (a)–(c) may be performed through open or minimally invasive surgical techniques. Preferably, the anchor is caused to rotate by a simple, non-rotational motion of the emplacement tool.

The insertion hole may e a pre-made borehole or may be an aperture formed by the anchor member or the emplacement tool during the step of inserting.

Other features and advantages of the present invention will become apparent from the following description of the invention which refers to the accompanying drawings.

BRIEF DESCRIPTION OF THE DRAWING(S)

The invention will now be described in greater detail in the following detailed description with reference to the drawings in which:

FIGS. 1A, B, C, D and E show steps in the insertion of an anchor according to a first embodiment of the invention;

FIGS. 2A and B shows steps in insertion of a second embodiment of an anchor according to the present invention;

FIGS. 3A, B, C, D and E show steps in the insertion of a third embodiment of an anchor according to the invention;

FIG. 4 is an isometric view of the anchor according to the third embodiment;

FIG. 5 is a side view of the anchor according to the third embodiment;

FIG. 6 is a top view of the anchor according to the third embodiment prior to deployment;

FIG. 7 is a top view of the anchor according to the third embodiment during deployment;

Figure 9:
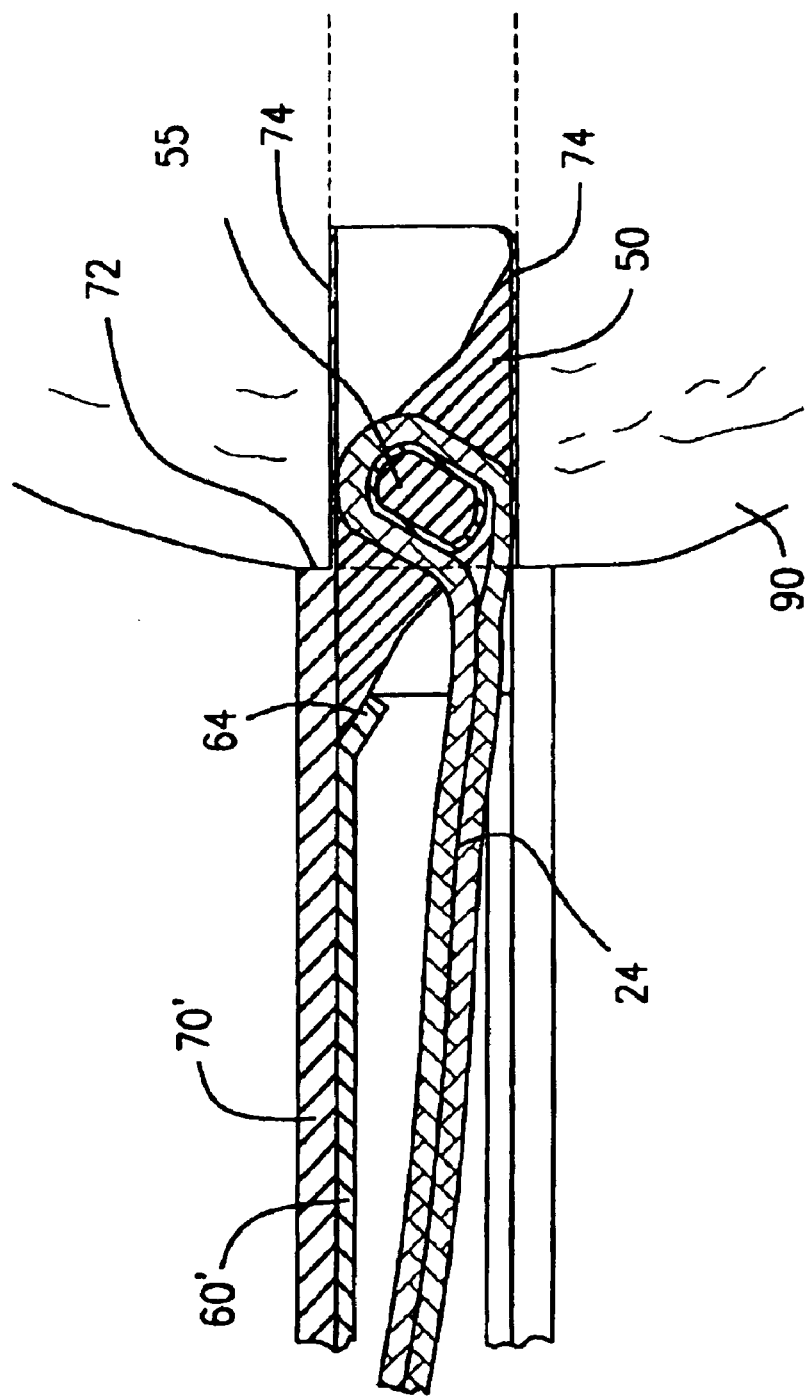
Figure 10:
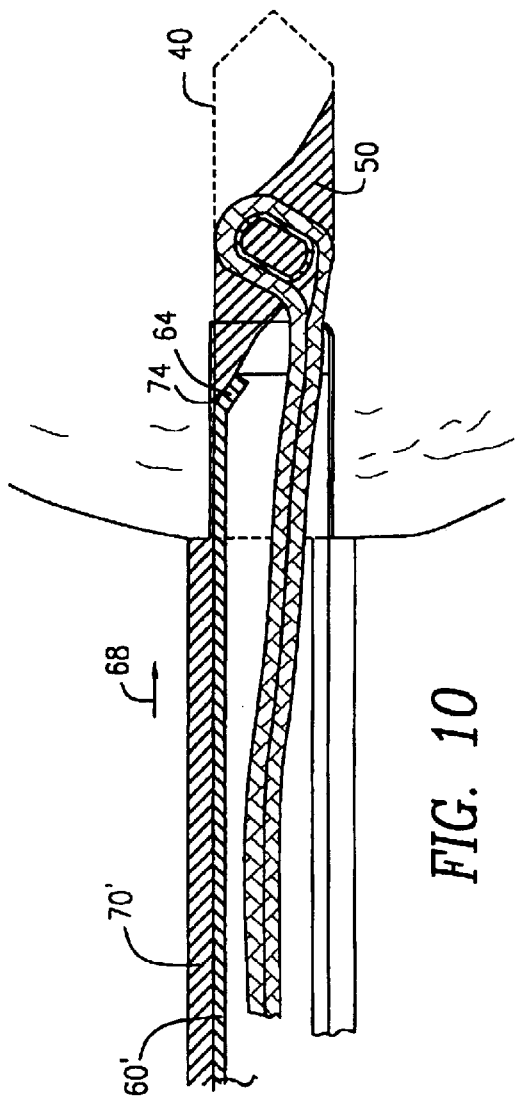
Figure 11:
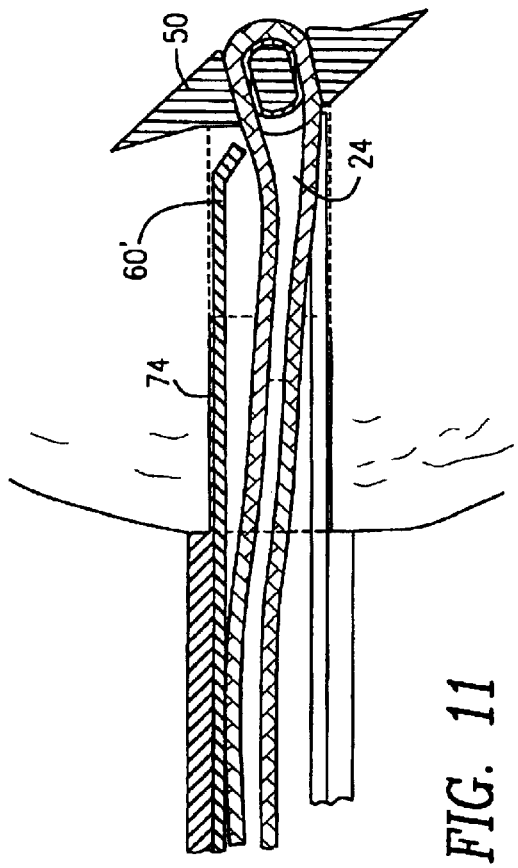

FIGS. 8A, B, C, D and E are progressive views of the anchor viewed proximally along the bone hole axis showing the anchor during different stages of deployment; and FIGS. 9, 10 and 11 shows details of the distal end of a tool for installing the anchor according to the third embodiment in a pre-deploy, mid-deploy and full deploy positions, respectively.

DETAILED DESCRIPTION OF EMBODIMENTS OF THE INVENTION

With reference now to the drawings, FIGS. 1A, B, C, D and E show an apparatus comprising the distal end 10 of an insertion tool 10', either disposable or reusable, with an anchor 20 attached thereon and inserted into a predrilled bone hole 40. The details of the remainder of the tool 10' are only shown schematically. Once inserted into the bone, the anchor 20 is flipped outwardly by the biasing force of a push member 22 (FIG. 1B) until the anchor reaches an approximately perpendicular position relative to the bone hole, as shown in FIGS. 1D and 1E. Push member 22 can be driven by another member that is actuated at a proximally located handle of the tool 10'. Alternatively, the push member 22 may be a spring-like member. In the embodiment shown, the member 22 has a spring characteristic, as shown in FIG. 1D, allowing the member to deflect when the tool is withdrawn. The pusher member 22 can also be a spring member whose spring provided biasing force causes the initial outward rotation of the anchor 20. After full deployment, the tool 10' is thereafter removed, as shown in FIG. 1E, leaving the anchor 20 in position, as shown, approximately aligned perpendicular to the axis of the tool 10' and borehole, with suture 24 looped around an internal passage or passages of the anchor. The anchor has been set initially by the force of the pusher member 22. The pusher member is released by a suitable actuating force (e.g. depressing a button on tool 10'). No rotation of the tool was required to set the anchor. See FIGS. 1A, B, C and D.

In the embodiment of FIGS. 1A, B, C, D and E, once the anchor is seated in the bone hole, the pusher member 22 is activated to flip the proximal end 23 of the anchor outwardly into the wall of the bone hole. Distal end 23A likewise penetrates into the bone hole as the anchor 20 rotates about axle 26. Edges 28 and 29 of the anchor 20 are provided with sharp edges to facilitate penetration into the bone hole. With an outward bias of the proximal end 23 of the anchor, the anchor will begin deploying to a horizontal position as the anchor and insertion tool assembly is withdrawn proximally from the bone hole as shown by arrow 27 in FIGS. 1C and 1D. Once the anchor has reached the approximately horizontal position relative to the axis of the bone hole, as shown in FIG. 1D, the anchor is separated from the insertion tool, leaving a secured anchor and suture 24 with which to reattach soft tissue. See FIG. 1E. The anchor 20 can be separated from the tool by causing forked distal end 10 of tool 10' to spread apart, away from ends of axle 26. Alternatively, forked distal ends 10 of tool 10' can have projections that are received in recesses in the anchor member located at opposite ends of axle 26. The projections are caused to move apart, thereby withdrawing them from the recesses and allowing the tool to be removed. As another alternative, axle 26 can be made of two spring biased sections that move oppositely horizontally in the pivot holes under bias of a tension spring, allowing the tool to be removed. Alternatively, the tool and anchor can be caused to separate automatically upon exertion of a predefined withdrawal force, such as by providing a frangible or breakable connection between tool and anchor that ruptures upon application of a predefined withdrawal force.

Figure 2B:
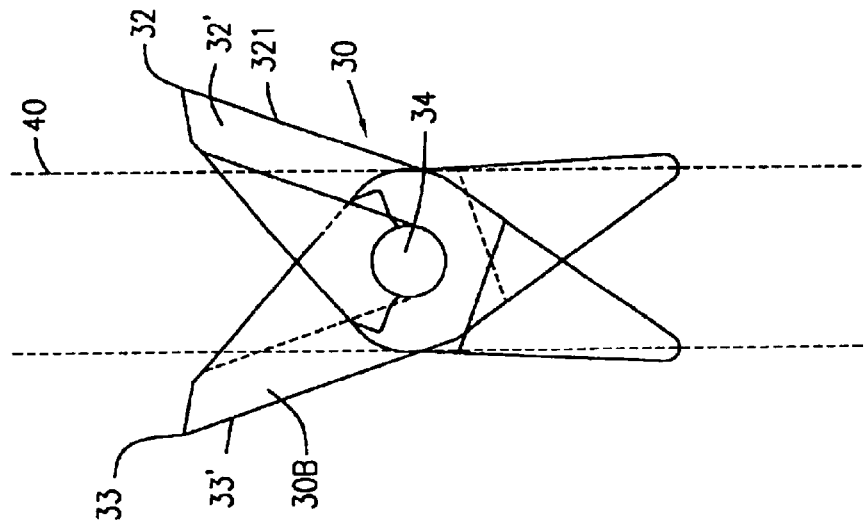
Figure 2A:
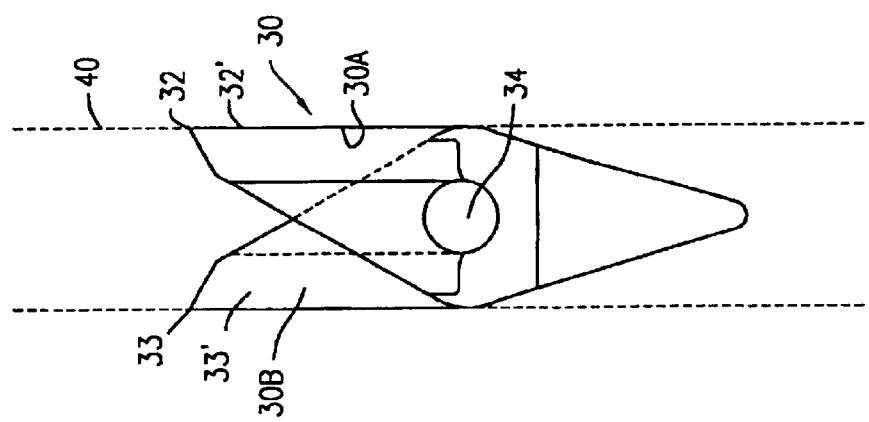

FIGS. 2A and B show a multi-piece anchor 30 in a bone hole in a predeployed state (FIG. 2A) and post deployed state (FIG. 2B). The anchor 30 is positioned in the bone hole and then actively deployed such that the proximal tips 32 and 33 of the anchor 30 are pushed outwardly and penetrate into the bone as the anchor is pulled proximally. In the embodiment of FIGS. 2A and B, the anchor 30 has two elements 30A and 30B disposed on a common shaft 34. The two elements are pushed by a pusher member (not shown) or by a spring like member (not shown) to cause the elements to pivot about the shaft and cut into the bore hole. Each member has a sharp edge 32', 33' to allow it to cut into the borehole.

In the embodiment of FIGS. 2A and 2B, the anchor is made from multiple parts as shown. This anchor 30 is intended to be attached to the distal end of an insertion tool which is not shown in the figures. Once the anchor is seated in the bone hole, a distally directed force is applied to the proximal ends of the anchor to bias the sharp edges 32' and 33' to engage into the wall of the bone hole. Upon partial withdrawal of the anchor and insertion tool assembly, the edges of the proximal ends 32 and 33 of the anchor will penetrate the bone walls and move the anchor members to an angle distinct from the axis of the bore hole. See FIG. 2B. Suture strands, not shown, are connected to the anchor at or near the pivot point 34 of the anchor with which soft tissue can be attached to the bone.

FIGS. 3A, B, C, D and E show stages of deployment of another embodiment of the anchor of the invention. The anchor itself is shown in FIGS. 4 to 7 and is formed approximately by slicing a cylinder in two parallel planes which are set at an angle to the long axis of the cylinder.

As shown in FIG. 4, this anchor 50 is formed approximately by slicing a portion of a cylinder along two parallel planes at an angle to the axis 51 of the cylinder, thereby forming surfaces having sharp edges 52 and 53. The cylinder section thus formed is provided with a center hub portion 55 having openings 57 and 58 surrounding the central hub portion. A suture 24 is threaded through the openings and around the hub portion 55. As shown in FIGS. 3A, B, C, D and E, a pusher member 60 is disposed in a cylinder 70 of the insertion tool 10; shown only schematically. The anchor is initially disposed at the distal end of the cylinder 70, inside a portion 74 of cylinder 70 of decreased wall thickness. Sutures 24 are wrapped around the center hub 55 of the anchor as shown. The pusher member 60 pushes the anchor 50 out of the cylinder 70 into the bore hole. Once the anchor has passed beyond the distal end of the cylinder, the pusher member 60 causes the anchor to pivot about its center. As shown in FIG. 3B, the pusher member 60 may have a rounded end 62. Once the anchor clears the cylinder, the sharp edges begin to cut into the bore hole as shown in FIG. 3C as force is applied by the pusher member 60. Upon further movement of the pusher member, the anchor attains the position shown in FIG. 3C, which is adequate deployment. At this point, the insertion tool 10' is removed as shown in FIG. 3D, and an upward tug can optionally be provided to the sutures to ensure that the anchor is secured as shown in FIG. 3E. Such tugging is only optional and is a good check to ensure that the anchor is secure. It may further cause some additional rotation of the anchor, as shown in FIG. 3E, although such further rotation is not required. The anchor is adequately set in the position shown in FIG. 3D. An advantage of this design is that the anchor 50 is not attached to the tool, so that separation occurs simply upon withdrawal of the tool.

FIGS. 4, 5, 6 and 7 shows various views of the anchor. In particular, FIG. 4 shows an isometric view. FIG. 5 shows a side view. FIG. 6 shows a top view of the anchor as it is disposed in the cylinder prior to deployment and FIG. 7 shows the anchor in a top view after full deployment. FIGS. 8A, B, C, D and E correspond to FIGS. 3A, B, C, D and E and show the anchor in the various stages of deployment, viewed from a proximal location.

FIG. 9 shows the anchor 50 according to the third embodiment and the preferred embodiment of the distal end of a tool for deploying the anchor 50. The distal end of the tool includes an outer tube 70' and an inner tube 60'. Tube 60' functions as a pusher member. The inner tube 60' has an end 64 which is formed at an angle to conform to the angled surface of the anchor 50. The suture 24 is looped around the center hub 55 of the anchor 50. The outer tube 70' has a stop shoulder 72 and at the distal end having a reduced diameter portion 74. The stop shoulder 72 functions as a stop for limiting movement of the outer tube 70' into the borehole in the bone surface indicated at 90. Once the stop shoulder 72 is seated on the bone surface 90, as shown in FIG. 10, the pusher member 60' is moved in the direction of arrow 68 and the anchor is pushed into the borehole, shown at 40. The anchor 50 is still maintained in the same orientation due to its abutting against the reduced diameter portion 74 and the angled end 64 of pusher member 60'.

As shown in FIG. 11, once the anchor 50 has cleared the reduced diameter portion 74 of the tube 70', further movement of the pusher member 60' causes the anchor 50 to rotate as shown to a position approximately perpendicular to the axis of the tool and borehole. The tool can then be removed and a tug applied to the suture 24 to ensure that it is set properly.

The anchor member of the embodiments shown may be shaped as a disk, oval, blade, kidney, be pointed, polygonal, or have any symmetrical or asymmetrical geometrical shape or be a solid or have fenestrations. The anchor member may have sharp edges, points, protrusions, cut outs, curves or other defining features. Also, the anchor member may be two dimensional or three dimensional. Additionally, the anchor member may be made from metal, a polymer, a bioabsorbable material, bone, or any other biocompatible material.

To insert the anchor, a hole in the bone may or may not need to be pre-made or pre-drilled, depending on the sharpness of the leading point of the anchor or tool, or whether there may be cutting surfaces, such as threads, on the anchor.

The insertion tool may be designed for a single use, i.e., disposable, or as a reusable instrument. Also, the insertion tool may be designed for open or minimally invasive surgery. The activation element to initiate the outward bias of the anchor may be a spring, lever, rod or any other suitable design element. Near the distal end of the insertion tool may be a shoulder stop to indicate the maximum depth of anchor insertion into biological tissue for more precise and reliable engagement of the anchor. An advantage of the invention is that only a small insertion opening in the form of a predrilled bone hole is required to implant the anchor, thus minimizing the trauma to the biological tissue and enhancing the fixation capability of the anchor. Further, in some embodiments having a sharp pointed end, it may not be necessary to even pre-form a hole.

Another advantage of the anchor and insertion tool assembly is that it may be provided as a single use device, in which case, it can be made with simplicity and provides convenience. Further, the anchor is set by simple motions, i.e., vertical insertion of the tool, depression of a button or other member to activate the biasing spring 22 and/or withdrawal of the tool. Rotation of the tool is not necessary to set the anchor.

Although the present invention has been described in relation to particular embodiments thereof, many other variations and modifications and other uses will become apparent to those skilled in the art. Therefore, the present invention should be limited not by the specific disclosure herein, but only by the appended claims.

What is claimed is:

1. An anchor for securement in biological tissue comprising:
    an anchor member adapted to be held by an insertion tool, the insertion tool having a longitudinal axis, the anchor member being rotatable about a first axis perpendicular to the longitudinal axis;
    the anchor member having a surface for engagement by the insertion tool for causing a rotational movement of the anchor member about the first axis whereby the anchor member engages the tissue at the site by moving about the first axis from a position substantially aligned with the longitudinal axis to a second position at an angle relative to the longitudinal axis, without requiring rotation about the longitudinal axis of the insertion tool, further wherein the anchor member comprises a member formed by slicing a cylinder along two parallel planes disposed at an acute angle to a longitudinal axis of the cylinder, thereby forming two parallel surfaces having sharp edges, the cylinder having a substantially cylindrical side surface, the surface of the anchor member for engagement by the insertion tool comprising a portion of the substantially cylindrical side surface of the cylinder, further wherein the anchor member has a central hub having an axis perpendicular to the longitudinal axis of the cylinder, the central hub being provided for looping a suture thereabout.

2. The anchor of claim 1, wherein the second position includes positions ranging from a position defined by an acute angle to the longitudinal axis of the insertion tool to a position perpendicular to the longitudinal axis.

3. The anchor of claim 1, further wherein the anchor is adapted to be received in a preformed borehole at the site to receive the anchor member.

4. The anchor of claim 1, further comprising a biasing element that applies a biasing force to cause the rotational movement.

5. The anchor of claim 4, wherein the biasing element comprises a pusher member of the insertion tool to apply the biasing force to the anchor member to cause the anchor member to engage the tissue at the site.

6. The anchor of claim 5, wherein the insertion tool further comprises a tubular member in which the pusher member and the anchor member are disposed; the pusher member moving relative to the tubular member to eject the anchor member into a borehole of the tissue with further relative movement of the pusher member causing the rotational movement.

7. The anchor of claim 6, further comprising a suture connected to the anchor member, the suture being capable of being tugged to ensure that the anchor member is secured in the borehole.

8. The anchor of claim 1, further wherein said anchor member comprises a rotational member having at least one cutting edge for cutting into the borehole.

9. The anchor of claim 8, wherein the anchor member has two cutting edges on opposite sides of a central hub about which the rotational movement occurs.

10. An anchor system for securement of an anchor in biological tissue comprising:

an insertion tool;

an anchor member adapted to be held by the insertion tool having a longitudinal axis, the anchor member being rotatable about a first axis perpendicular to the longitudinal axis;

the anchor member having a surface for engagement by the insertion tool for causing a rotational movement of the anchor member about the first axis whereby the anchor member engages the tissue at the site by moving about the first axis from a position substantially aligned with the longitudinal axis to a second position at an angle relative to the longitudinal axis, without requiring rotation about the longitudinal axis of the insertion tool, further comprising a biasing element that applies a biasing force to cause the rotational movement;

wherein the biasing element comprises a pusher member of the insertion tool that applies the biasing force to the anchor member to cause the anchor member to engage the tissue at the site;

further wherein the insertion tool further comprises a tubular member in which the pusher member and the anchor member are disposed; the pusher member moving relative to the tubular member to eject the anchor member into a borehole of the tissue with further relative movement of the pusher member causing the rotational movement; and wherein the pusher member has a substantially hemispherical distal end for engaging the anchor member and causing the rotational movement.

11. An anchor for securement in biological tissue comprising:

an anchor member adapted to be held by an insertion tool, the insertion tool having a longitudinal axis, the anchor member being rotatable about a first axis perpendicular to the longitudinal axis;

the anchor member having a surface for engagement by the insertion tool for causing a rotational movement of the anchor member about the first axis whereby the anchor member engages the tissue at the site by moving about the first axis from a position substantially aligned with the longitudinal axis to a second position at an angle relative to the longitudinal axis, without requiring rotation about the longitudinal axis of the insertion tool, further wherein the anchor member comprises a member formed by slicing a cylinder along two parallel planes disposed at an acute angle to a longitudinal axis of the cylinder, thereby forming two parallel surfaces having sharp edges, the cylinder having a substantially cylindrical side surface, the surface of the anchor member for engagement by the insertion tool comprising a portion of the substantially cylindrical side surface of the cylinder;

further comprising a pusher member of the insertion tool for applying a biasing force to the anchor member to cause the anchor member to engage the tissue at the site;

wherein the insertion tool further comprise a tubular member in which the pusher member and the anchor member are disposed the pusher member moving relative to the tubular member to eject the anchor member into a borehole of the tissue with further relative movement of the pusher member causing the rotational movement; and wherein the pusher member has an angled surface at a distal end thereof for holding the anchor member in a fixed orientation in the tubular member prior to ejection of the anchor member from the tubular member.

12. An anchor system for securement of an anchor in biological tissue comprising:

an insertion tool;

an anchor member adapted to be held by the insertion tool, the insertion tool having a longitudinal axis, the anchor member being rotatable about a first axis perpendicular to the longitudinal axis;

the anchor member having a surface for engagement by the insertion tool for causing a rotational movement of the anchor member about the first axis whereby the anchor member engages the tissue at the site by moving about the first axis from a position substantially aligned with the longitudinal axis to a second position at an angle relative to the longitudinal axis, without requiring rotation about the longitudinal axis of the insertion tool, further comprising a biasing element that applies a biasing force to cause the rotational movement;

wherein the biasing element comprises a pusher member of the insertion tool that applied the biasing force to the anchor member to cause the anchor member to engage the tissue at the site;

further wherein the insertion tool further comprises a tubular member in which the pusher member and the anchor member are disposed; the pusher member moving relative to the tubular member to eject the anchor member into a borehole of the tissue with further relative movement of the pusher member causing the rotational movement; and wherein the tubular member has a shoulder defining a portion of a wall of the tubular member of decreased thickness, the portion of the wall of decreased thickness being adapted to be inserted into the borehole with the shoulder defining a stop for the insertion of the insertion tool into the borehole.

13. The anchor system of claim 12, wherein the pusher member has a substantially hemispherical distal end for engaging the anchor member and causing the rotational movement.

14. An anchor system for securement of an anchor in biological tissue comprising:

an insertion tool;

an anchor member adapted to be held by the insertion tool, the insertion tool having a longitudinal axis, the anchor member being rotatable about a first axis perpendicular to the longitudinal axis;

the insertion tool comprising a tubular member and a pusher member slidably mounted concentrically therein;

the anchor member having a surface for engagement by the pusher member of the insertion tool for causing a rotational movement of the anchor member about the first axis whereby the anchor member engages the tissue at the site by moving about the first axis from a position substantially aligned with the longitudinal axis to a second position at an angle relative to the longitudinal axis, without requiring rotation about the longitudinal axis of the insertion tool, further wherein the anchor member comprises a member formed by slicing a cylinder along two parallel planes disposed at an acute angle to a longitudinal axis of the cylinder, thereby forming two parallel surfaces having sharp edges, the cylinder having a substantially cylindrical side surface, the surface of the anchor member for engagement by the pusher member of the insertion tool comprising a portion of the substantially cylindrical side surface of the cylinder; and further wherein the pusher member has an angled surface at a distal end thereof for holding the anchor member in a fixed orientation in the tubular member prior to ejection of the anchor member from the tubular member.

15. The anchor system of claim 14, further wherein the anchor member has a central hub about which a suture is looped.

16. The anchor system of claim 14, wherein the second position includes positions ranging from a position defined by an acute angle to the longitudinal axis of the insertion tool to a position perpendicular to the longitudinal axis.

17. The anchor system of claim 14, further wherein the anchor is adapted to be received in a preformed borehole at the site to receive the anchor member.

18. The anchor system of claim 14, wherein the pusher member moves relative to the tubular member to eject the anchor member into a borehole of the tissue with further relative movement of the pusher member causing the rotational movement.

19. The anchor system of claim 14, further comprising a suture connected to the anchor member, the suture being capable of being tugged to ensure that the anchor member is secured in the borehole.

20. The anchor system of claim 14, further wherein said anchor member comprises a rotational member having at least one cutting edge for cutting into the borehole.

21. The anchor system of claim 20, wherein the anchor member has two cutting edges on opposite sides of a central hub about which the rotational movement occurs.

22. An anchor system for securement of an anchor in biological tissue comprising:

an insertion tool;

an anchor member adapted to be held by the insertion tool, the insertion tool having a longitudinal axis, the anchor member being rotatable about a first axis perpendicular to the longitudinal axis;

the anchor member having a surface for engagement by the insertion tool for causing a rotational movement of the anchor member about the first axis whereby the anchor member engages the tissue at the site by moving about the first axis from a position substantially aligned with the longitudinal axis to a second position at an angle relative to the longitudinal axis, without requiring rotation about the longitudinal axis of the insertion tool, further wherein the anchor member comprises a member formed by slicing a cylinder along two parallel planes disposed at an acute angle to a longitudinal axis of the cylinder, thereby forming two parallel surfaces having sharp edges, the cylinder having a substantially cylindrical side surface, the surface of the anchor member for engagement by the insertion tool comprising a portion of the substantially cylindrical side surface of the cylinder;

further comprising a biasing element that applies a biasing force to cause the rotational movement;

wherein the biasing element comprises a pusher member of the insertion tool that applies the biasing force to the anchor member to cause the anchor member to engage the tissue at the site;

further wherein the insertion tool further comprises a tubular member in which the pusher member and the anchor member are disposed; the pusher member moving relative to the tubular member to eject the anchor member into a borehole of the tissue with further relative movement of the pusher member causing the rotational movement; and wherein the pusher member is substantially hollow and has a distal end having an angled portion for holding the anchor member in a fixed orientation in the tubular member prior to ejection of the anchor member from the tubular member and further wherein the angled portion engages the anchor member and causes the rotational movement.

* * * * *